United States Patent [19]

Brandes et al.

[11] Patent Number: 4,518,605

[45] Date of Patent: May 21, 1985

[54] FUNGICIDAL AZOLE-SUBSTITUTED OXIMINO-CYANO-ACETAMIDE DERIVATIVES

[75] Inventors: Wilhelm Brandes, Leichlingen; Werner Daum, Krefeld, both of Fed. Rep. of Germany

[73] Assignee: Bayer Aktiengesellschaft, Leverkusen, Fed. Rep. of Germany

[21] Appl. No.: 500,732

[22] Filed: Jun. 3, 1983

[30] Foreign Application Priority Data

Jun. 19, 1982 [DE] Fed. Rep. of Germany ....... 3222961

[51] Int. Cl.$^3$ .................... A01N 43/50; A01N 43/64; C07D 233/61; C07D 249/08
[52] U.S. Cl. .................... 514/383; 548/262; 548/341; 514/399
[58] Field of Search ................ 548/262, 341; 424/269, 424/273 R

[56] References Cited

U.S. PATENT DOCUMENTS

| | | | |
|---|---|---|---|
| 3,919,284 | 11/1975 | Lin | 260/465.4 X |
| 3,957,847 | 5/1976 | Davidson | 260/465.4 |
| 4,188,401 | 2/1980 | Brandes et al. | . |
| 4,344,953 | 8/1982 | Stetter et al. | 548/378 |
| 4,359,469 | 11/1982 | Stetter et al. | 548/378 |
| 4,368,202 | 1/1983 | Brandes et al. | 548/378 |

FOREIGN PATENT DOCUMENTS 0005249 11/1979 European Pat. Off. ............ 548/262
0051784 5/1982 European Pat. Off. ........ 424/273 P
2312956 9/1973 Fed. Rep. of Germany ... 260/465.4

Primary Examiner—Alton D. Rollins
Attorney, Agent, or Firm—Sprung, Horn, Kramer & Woods

[57] ABSTRACT

Fungicidally active novel azole-substituted oximino-cyano-acetamide derivatives of the formula

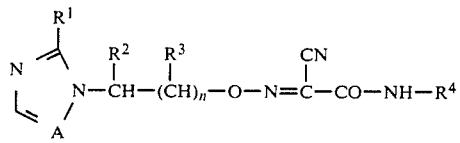

in which
$R^1$ and $R^3$ each independently is hydrogen or alkyl having up to 3 carbon atoms,
$R^2$ is hydrogen, alkyl having up to 6 carbon atoms, or halogenoalkyl having up to 2 carbon atoms and up to 5 halogen atoms,
$R^4$ is hydrogen or CO—NH—$R^5$,
$R^5$ is hydrogen, cycloalkyl having 3 to 7 carbon carbon atoms, or alkyl having up to 8 carbon atoms and optionally substituted by cyano, hydrocarbonyl, aminocarbonyl, alkoxy and/or alkoxycarbonyl, each having up to 4 carbon atoms in the alkyl part,
A is N or CH, and
n is 0 or 1.

11 Claims, No Drawings

FUNGICIDAL AZOLE-SUBSTITUTED OXIMINO-CYANO-ACETAMIDE DERIVATIVES

The present invention relates to new azole-substituted oximino-cyano-acetamide derivatives, several processes for their preparation and their use as fungicides.

As has already been known for a long time, in particular zinc ethylene-1,2-bis-dithiocarbamate and N-trichloromethylthio-tetrahydrophthalimide are used as fungicides in agriculture and in horticulture; among the commercial products, the stated compounds are of great importance (see R. Wegler, "Chemie der Pflanzenschutzund Schädlingsbekämpfungsmittel" [Chemistry of Plant Protection Agents and Pest-Combating Agents], volume 2, pages 65 and 108, Berlin/Heidelberg/New York (1970)). However, the action is not always satisfactory when low concentrations are used. Furthermore, these fungicides cannot be employed curatively.

It is also known from a number of patent specifications that some isonitroso-cyano-acetamide derivatives have a fungicidal action (in this context see, for example, German Offenlegungsschrift [German Published Specification] No. 2,312,956 and U.S. Pat. Nos. 3,919,284, 3,957,847 and 4,188,401). In the case of these compounds also, the activity is not always reliable when low amounts are used, and toleration by plants is not always completely satisfactory in the case of normal concentrations.

The azole-substituted oximino-cyano-acetamide derivatives of the general formula

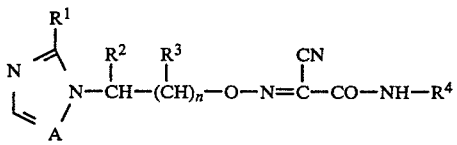

in which $R^1$ and $R^3$ represent hydrogen and alkyl having up to 3 carbon atoms, $R^2$ represents hydrogen, alkyl having up to 6 carbon atoms and halogenoalkyl having up to 2 carbon atoms and up to 5 halogen atoms, $R^4$ represents hydrogen and the group CO—NH—$R^5$, wherein $R^5$ represents hydrogen, cycloalkyl having 3 to 7 and alkyl having up to 8 carbon atoms, it being possible for the latter to be substituted by cyano, hydroxycarbonyl, aminocarbonyl, alkoxy and alkoxycarbonyl groups, each having up to 4 carbon atoms in the alkyl part, A represents N or the CH group and n represents the numbers 0 or 1, have now been found as new substances.

The substances according to the invention, of the general formula (I), can be present as oxime derivatives in 2 different geometric structures:

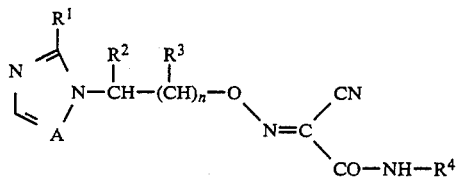

E derivative

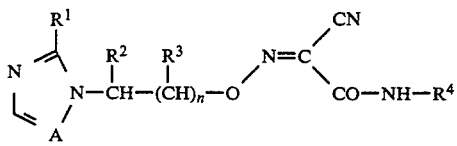

Z derivative

The three-dimensional structure will not be described below; for the purposes of the present application, the formulae given are intended in any case also to include the corresponding formula of the E or Z geometric structure.

Furthermore, it has been found that the azole-substituted oximino-cyano-acetamide derivatives of the formula (I) are obtained when (a) an N-alkylazole of the formula

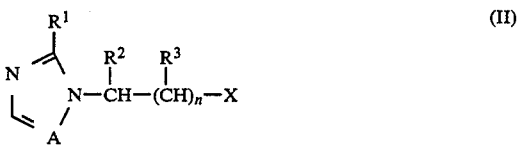

in which $R^1$, $R^2$, $R^3$, A and n have the meanings given above and

X represents a leaving group, such as chlorine, bromine, iodine or a sulphonyloxy group, or its salt (such as, for example, the hydrohalide), is reacted with a 2-oximino-2-cyano-acetamide derivative of the formula

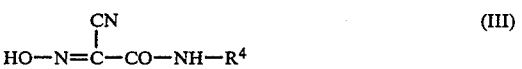

in which $R^4$ has the abovementioned meaning, in the presence of an acid-binding agent; or (b) those azole-substituted oximino-cyano-acetamide derivatives of the formula (I), in which $R^4$ represents the CO—NH—$R^5$ group, wherein $R^5$ has the abovementioned meanings, with the exception of hydrogen and hydroxycarbonylalkyl, are also obtained when compounds according to the invention, prepared according to process (a) and of the formula

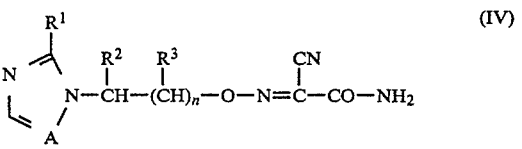

in which $R^1$, $R^2$, $R^3$, A and n have the abovementioned meanings, (formula (IV) is identical to formula (I) if the substituent $R^4$ in formula (I) represents hydrogen), is reacted with an isocyanate of the formula $$OCN-R^5 \qquad (V)$$

in which $R^5$ has the abovementioned meanings, with the exception of hydrogen and hydroxycarbonylalkyl, in the presence of a strong base; and finally, according to a further process variant (c) for the preparation of those compounds of the formula (I) in which $R^4$ represents $CO-NH-R^5$ and $R^5$ has the meaning of alkyl-carbonyloxyalkyl in this formula, a carboxylic acid synthesized by process (a) of the formula

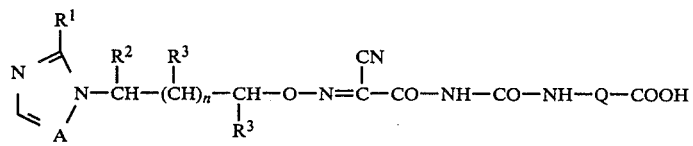

(VI)

in which $R^1$, $R^2$, $R^3$, A and n have the abovementioned meanings and

Q represents straight or branched alkylene having 1 to 8 carbon atoms, (the compounds of the formula (VI) are identical to the compounds of the formula (I) if the substituent $R^4$ in formula (I) represents the $CO-NH-R^5$ group and $R^5$ has the meaning of hydroxycarbonylalkyl in this formula), in the form of its alkali metal, alkaline earth metal or ammonium salt, is reacted with an alkylating agent of the formula $$Y-R^6 \qquad (VII)$$

in which $R^6$ represents alkyl having 1 to 4 carbon atoms and

Y represents a leaving group, such as chlorine, bromine, iodine, alkoxysulphonyloxy, alkylsulphonyloxy or arylsulphonyloxy.

The new azole-substituted oximino-cyano-acetamide derivatives possess powerful fungicidal properties. They can be used protectively, curatively and even eradicatively, and in addition have systemic and/or locosystemic properties. Surprisingly, they exhibit better toleration by plants than the isonitrosocyanoacetamide derivatives known from the prior art. Compared with the dithiocarbamates and N-trichloromethylthio-tetrahydrophthalimide, they possess the advantage of curative and eradicative action.

Because of the many possible uses of their superior biological properties, the compounds according to the invention represent a valuable enrichment of the art.

Among the azole-substituted oximino-cyano-acetamide derivatives according to the invention of the formula (I), preferred compounds are those in which $R^1$ and $R^3$ represent hydrogen and methyl, $R^2$ represents hydrogen and alkyl having 1 to 4 carbon atoms, $R^4$ represents hydrogen and the $CO-NH-R^5$ group, wherein $R^5$ represents hydrogen, cycloalkyl having 3 to 6 carbon atoms and alkyl which has 1 to 5 carbon atoms and is optionally substituted by cyano or alkoxy groups having up to 4 carbon atoms, and A and n have the meanings given in the definition of the invention.

Particularly preferred compounds of the formula (I) are those in which $R^1$ and $R^3$ represent hydrogen, $R^2$ represents hydrogen, methyl, ethyl, isopropyl and tert.-butyl, and $R^4$ has the abovementioned preferred meanings, $R^5$ representing hydrogen, methyl, ethyl, n-propyl and isopropyl.

If, for example, 1-chloroethyl-triazole hydrochloride and 1-(2-oximino-2-cyano-acetyl)-3-ethyl-urea are used, according to process variant (a), as starting materials for the preparation of the compounds according to the invention of the general formula (I), and ethyl-diisopropylamine is used as a proton acceptor, the course of the reaction can be represented by the following equation:

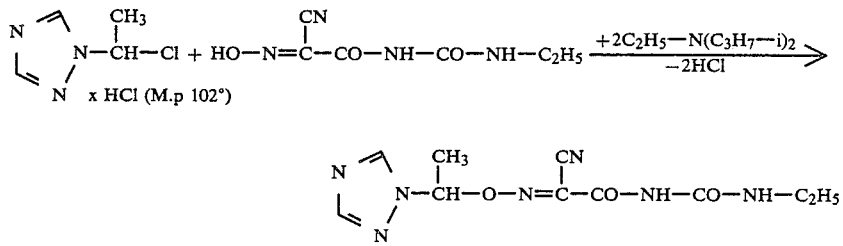

If 1-triazol-1-yl-2-(benzenesulphonyloxy)propane and the potasium salt of 2-oximino-2-cyano-acetamide are used as starting materials in the case in which the reaction is carried out in the presence of an inorganic base, the course of the reaction can be represented by the following equation:

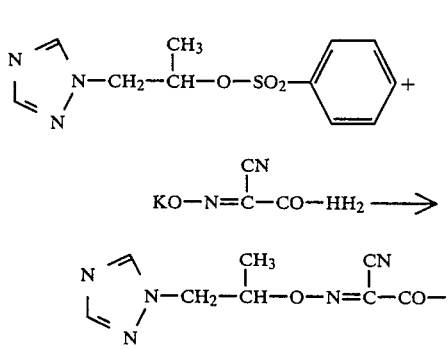

-continued

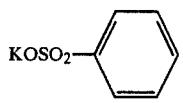

If, for example, 2-(triazol-1-yl-methyl-oximino)-2-cyano-acetamide, sodium hydride and n-butyl isocyanate are used as starting materials according to process variant (b), the course of the reaction can be represented by the following equation:

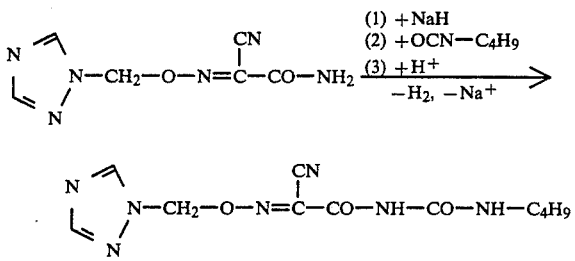

If, for example, 1-[2-(triazol-1-yl-methyl-oximino)-2-cyano-acetyl]-3-[5-(hydroxycarbonyl)-pentyl]-urea, in the form of its sodium salt, and methyl iodide are used as starting materials according to process variant (c), the course of the reaction can be represented by the following equation:

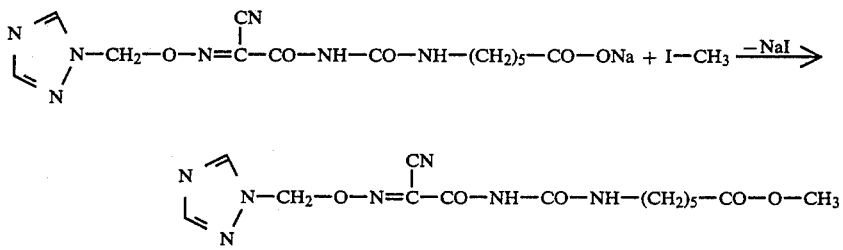

Formula (II) gives a definition of the N-alkyl-azoles required as starting substances according to process variant (a). In this formula, $R^1$, $R^2$, $R^3$, A and n preferably represent those radicals which have already been mentioned in connection with the preferred substituent meanings for formula (I).

Some of the compounds of the formula (II) are known (Chem. Abstr. 93, 46,530 (1980)). Those compounds of the formula (II) in which the index n has the value of 0 can be prepared in close analogy to the data given in the literature (J. Chem. Soc. 1960, 5,272 and DE-OS [German Published Specification] No. 2,835,158), for example by a method wherein an aldehyde is brought to reaction with an azole, if appropriate in the presence of a solvent, and the methylol compound obtained is then reacted with a thionyl halide, the N-alkylazoles (II) then being obtained in most cases as hydrohalides.

The following compounds may be mentioned as examples here: 1-chloromethyl-, 1-(1-chloroethyl)-, 1-(1,2-dichloroethyl)-, 1-(1-chloro-2-methyl-propyl)- and 1-(1-chlorobutyl)-triazole hydrochloride, 1-(1-bromoethyl)-triazole hydrobromide and 1-chloromethyl-, 1-(1-chloroethyl)-, 1-(1,2-dichloroethyl)-, 1-(1-chloro-2-methylpropyl)- and 1-(1-chloropentyl)-imidazole and -2-methylimidazole hydrochloride.

Those compounds of the formula (II) in which n represents 1 can be obtained, for example, from 2-(hydroxyalkyl)-azoles by reaction with sulphonyl chlorides and tertiary amines or alkali metal hydrides.

The following may be mentioned as examples of compounds of the formula (II) in which n represents 1: 2-(triazol-1-yl)-, 2-(imidazol-1-yl)- and 2-(2-methylimidazol-1-yl)-ethyl-methanesulphonates and the corresponding benzenesulphonates, p-toluenesulphonates and p-chlorobenzenesulphonates, and also the compounds 1-(triazol-1-yl)-2-(benzenesulphonyloxy)-propane and 1-(imidazol-1-yl)-2-(4-chlorobenzenesulphonyloxy)butane.

The N-(hydroxyalkyl)-azoles mentioned further above are obtained by reaction of azoles with alkylene oxides, such as, for example, ethylene oxide, in toluene as a solvent, preferably at room temperature.

The 2-oximino-2-cyano-acetamide derivatives of the general formula (III) are furthermore required for the reactions according to the invention by process variant (a). Some of the compounds are known (see Chem. Ber. 42, 738–741 (1909); 54, 1,334 (1921); and U.S. Pat. No. 4,188,401). They are obtained, for example, when, in a first stage, ethyl isocyanate is reacted with ammonia to give N-ethyl-urea, and, in a second stage, this product is reacted with cyanoacetic acid in the presence of acetic anhydride, and the 1-ethyl-3-(2-cyano-acetyl)-urea thus obtained is oximated with nitrous acid.

The isocyanates of the formula (V) which are required for process variant (b) are generally known compounds; they are obtained in a customary manner when, for example, primary amines are reacted with phosgene.

In formula (V), $R^5$ preferably has those meanings which have been mentioned further above in the discussion of formula (I) as being preferred for $R^5$. The following isocyanates of the formula (V) may be mentioned:

methyl, ethyl, propyl, isopropyl, butyl, sec.-butyl, isobutyl, ω-cyanoethyl, 1-cyano-1-methyl-ethyl, ω-cyanopropyl, ω-cyanopentyl, methoxycarbonylmethyl, ethoxycarbonyl-methyl, propoxy-carbonylethyl, 1-methoxycarbonyl-1-methyl-ethyl, 1-ethoxycarbonyl-1-methyl-ethyl, ethoxycarbonyl-1-ethyl-ethyl, methoxycarbonyl-1-ethyl-ethyl, methoxycarbonyl-propyl, methoxycarbonylpentyl, isopropoxycarbonylpentyl, methoxymethyl, methoxyethyl, cyclopropyl, cyclopentyl and cyclohexyl isocyanate.

All organic solvents which are inert to the reactants are suitable diluents for the process according to variant (a); polar solvents are preferably used. Examples of such solvents which may be mentioned are acetonitrile, acetone, chloroform, benzonitrile, dimethylacetamide, dimethylformamide, dimethylsulphoxide, chlorobenzene, ethyl acetate, dioxane, methyl ethyl ketone, methylene chloride and tetrahydrofuran.

The reactions can also be carried out in mixtures of water and a water-miscible organic solvent, or in heterogeneous systems consisting of water and a solvent which is immiscible or only partially miscible with water.

Either organic bases, preferably tertiary amines, such as, for example, quinoline, dimethylbenzylamine, dimethylaniline, ethyldicyclohexylamine, ethyldiisopropylamine, piccoline, pyridine and triethylamine, are used as acid-binding agents for the reaction according to process (a), or an alkali metal salt or alkaline earth metal salt of the 2-oximino-2-cyano-acetamide derivative in an inert solvent is initially introduced, or the salt is produced by adding a caustic alkali solution, alcoholates or an alkaline earth metal hydroxide to a mixture of the 2-oximino-2-cyano-acetamide derivative and a high-boiling solvent and then carefully removing water or distilling off the alcohol.

The reaction temperatures and the duration of the reaction in process (a) are determined by the activity of the starting materials. In general, the reaction is carried out at between about $-50°$ and $+80°$ C., preferably between $-30°$ and $+40°$ C. When water is used, or used concomitantly, as the diluent, the reaction is carried out in the temperature range between the solidification point of the aqueous solution and about $+60°$ C., preferably at $0°$ to $+40°$ C.

To carry out the process according to the invention by variant (a), the 2-cyano-2-oximino-acetamide derivative of the formula (III), dispersed or dissolved in the diluents mentioned, is initially introduced in stoichiometric amount, and a small excess of tertiary amine is added. It is also possible to introduce the N-alkylazole (II) into a mixture of the diluent and the alkali metal salt, alkaline earth metal salt or ammonium salt of the 2-cyano-2-oximino-acetamide derivative (III). When an N-alkylazole salt is used, a molar amount of a tertiary amine is again introduced either before addition of the azole compound or simultaneously with this addition.

The reaction mixture should give an alkaline reaction at the end of the reaction, but should be rendered slightly acidic soon thereafter.

According to a particular procedure, a small amount of an iodide is added to the mixtures before the beginning of the reaction if a compound of the formula (II) with iodine as a leaving group is not employed. This procedure increases the reaction rate.

Suitable diluents for the process according to variant (b) are inert anhydrous solvents, such as, for example, ethers, such as diisopropyl ether, dioxane or tetrahydrofuran.

In process (b), the reaction temperatures can be varied between $-20°$ and $+80°$ C., but the reaction is preferably carried out at between $+20°$ and $60°$ C.

To carry out the process according to the invention by variant (b), a 2-cyano-2-(azol-1-yl-alkyl-oximino)-acetamide derivative of the formula (IV), in one of the inert solvents described in more detail above, is converted, using sodium hydride or potassium tert.-butylate, into the corresponding alkali metal salt, and the product is then reacted with the isocyanate of the formula (V) in the stated temperature range. After the reaction is complete, the cold mixture is rendered slightly acidic with an organic carboxylic acid.

Suitable diluents for the process according to variant (c) are all inert solvents. Acetonitrile, dioxane or ketones, such as, for example, acetone and diethyl ketone, may be preferably mentioned.

In process (c), the reaction temperatures can be varied between $-20°$ and $+80°$ C., but the reaction is preferably carried out at between $+20°$ and $60°$ C.

According to process (c), the 1-(2-cyano-2-(azol-1-yl-alkyl-oximino))-3-($\omega$-carboxyalkyl)-urea derivative obtained by process (a), of the formula (VI), in the stated solvents and after salt formation with an alkali metal or alkaline earth metal hydroxide or carbonate or with a tertiary amine, is reacted with an alkylating agent of the formula (VII).

Depending on the reaction conditions, the active compounds according to the invention are obtained in crystalline form, or remain dissolved in organic solution and can, after washing the solution with water, then be separated out by carefully evaporating down the solution or by adding slightly polar organic solvents, such as cyclohexane, dibutyl ether or carbon tetrachloride. If necessary, water-miscible polar solvents must be removed after the reaction by evaporating them off in vacuo.

If the compounds according to the invention are obtained dissolved in a water-miscible solvent, they can, if required, also be precipitated by the addition of water. If the particular conditions of the working-up process permit, the solutions of the active compounds according to the invention, or the still solvent-moist suspensions of the active compounds, are rendered slightly acidic.

Some compounds also have high solubility in water.

Some of the compounds according to the invention decompose at a relatively high temperature: in these cases, the melting points cannot be determined at all or can be determined only with low accuracy. The presence of certain structural elements is shown by the NMR spectra. The IR spectra also show characteristic absorption bands.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Oomycetes, for example against the blight and late blight of potato and tomato causative organism (*Phytophthora infestans*).

They exhibit a high curative and protective activity. In addition, good actions against rust fungi are found.

The active compounds according to the invention not only have the good properties of outstanding commercial preparations, but possess in addition substantial advantages. These are associated principally with the ability of the substances according to the invention to penetrate the plants. They can be absorbed by the seed surface, by the roots and also by above-ground plant organs after external applications. They also possess the advantageous ability to act locosystemically, that is to say to have an in-depth effect in the plant tissue and hence eliminate fungal pathogens which have already penetrated the tissue of the host plant.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

In addition to the above possible formulations, it should be noted that the substances according to the invention can be formulated together with sucrose, dextrose and dextrins, with anhydrous calcium sulphate or calcium sulphate hemihydrate, and with carboxylic acids, such as, for example, fumaric acid of 4-hydroxybenzoic acid, or even with weakly acidic ion exchangers.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

PREPARATION EXAMPLES

EXAMPLE 1

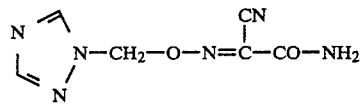

(Process a)

61.1 g (1 mol) of 1,2,4-triazole and 30 g (1 mol) of paraformaldehyde in 700 ml of alcohol-free chloroform are boiled under reflux for 4 hours. The solution obtained is filtered at room temperature, and the filtrate is added dropwise, in the course of 2 hours, to 250 g (2.1 mols) of thionyl chloride, while cooling with an ice/sodium chloride coolant mixture. The reaction mixture is allowed to stand for 17 hours, and then evaporated down in vacuo. The residue, 1-(chloromethyl)-1,2,4-triazole hydrochloride, crystallizes out on stirring with 800 ml of acetonitrile. It is directly processed further.

113 g (1 mol) of 2-cyano-2-oximinoacetamide is added to the mixture obtained above, and triethylamine is added dropwise at −2° C. until a sample of the reaction mixture with water shows a pH value of 9. The pH value is brought to about 5 to 7 by the addition of acetic acid. The precipitate of triethylamine hydrochloride is separated off, the solution is evaporated down in vacuo and the residue is treated with diethyl ketone to precipitate a further amount of triethylamine hydrochloride. The diethyl ketone solution is evaporated down in vacuo, and the residue is brought to crystallization by the addition of butyl alcohol. 68.7 g of 2-cyano-2-(1,2,4- triazol-1-yl-methoximino)-acetimide of melting point 156.5° C. are obtained; this is 36% of theory (including the intermediate stage).

EXAMPLE 2

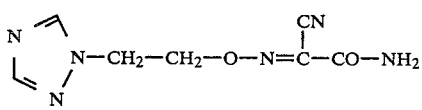

(Process a)

troduced at 51° to 54° C., and 22.6 g of 1-(2-hydroxyethyl)-1,2,4-triazole are introduced in the course of 30 minutes. The mixture is left for a further 90 minutes at this temperature. 38 g of p-toluenesulphonyl chloride are then introduced at −5° C. After the reaction is complete, the mixture is evaporated down in vacuo, and water is added to the residue. After drying, 1-(2-(p-toluenesulphonyloxy)-ethyl)-1,2,4-triazole can be triturated with petroleum ether. The yield is 34 g, and the melting point is 84° C.

The following compounds of the general formula (I) are obtained in a corresponding manner:

| Example 3: | ![structure] N—CH₂—O—N=C(CN)—CO—NH—CO—NH₂ (triazolyl) | M.p. 185–194° C. |
|---|---|---|
| Example 4: | N—CH(CH₃)—O—N=C(CN)—CO—NH₂ (triazolyl) | M.p. 130° C. |
| Example 5: | N—CH₂—O—N=C(CN)—CO—NH₂ (pyrazolyl) | M.p. 179° C. |
| Example 6: | N—CH(CH₃)—O—N=C(CN)—CO—NH—CO—NH—C₂H₅ (triazolyl) | M.p. 120.5° C. |
| Example 7: | N—CH(CH(CH₃)₂)—O—N=C(CN)—CO—NH₂ × H₂O (pyrazolyl) | hygroscopic H¹—NMR N—CH—O dδ = 5.83 ppm |
| Example 8: | N—CH₂—O—N=C(CN)—CO—NH₂ (3-methylpyrazolyl) | M.p. 160° C. |
| Example 9: | N—CH(C(CH₃)₃)—O—N=C(CN)—CO—NH₂ (triazolyl) | H¹—NMR N—CH—O sδ = 6.03 ppm viscous product |

15.1 g (0.1 mol) of the potassium salt of 2-cyano-2-oximinoacetamide and 28.3 g (0.106 mol) of 1-(2-(p-toluenesulphonyloxy)-ethyl)-1,2,4-triazole in 100 ml of acetonitrile are heated at 80° C. for 10 hours. The solid product is separated off, and the acetonitrile solution is evaporated down in vacuo. The residue is recrystallized from boiling diethyl ketone. 13.4 g of 2-cyano-2-[2-(1,2,4-triazol-1-yl)-ethyl-oximino]-acetamide of melting point 137° C. are obtained: this is 64% of theory.

Precursor

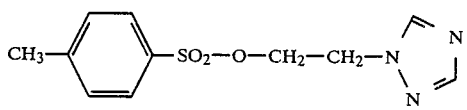

6.4 g of a 75 to 80% strength preparation of sodium hydride and 300 ml of tetrahydrofuran are initially infrom individual precursors of the general formula (II):

| | | |
|---|---|---|
| (triazole) | N—CH(CH₃)—Cl × HCl | M.p. (93–) 102° |
| (triazole) | N—CH₂Cl × HCl | extremely hygroscopic |
| (triazole) | N—CHCl(CH(CH₃)₂) × HCl | M.p. (138–) 154° C. |

EXAMPLE A

Phytophthora Test (tomato)/curative
Solvent: 4.7 parts by weight of acetone
Emulsifier: 0.3 parts by weight of alkyl-aryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous spore suspension of *Phytophthera infestans*. The plants remain in an incubation cabinet at 20° C. and 100% relative atmospheric humidity for 7 hours. After a short drying off time, the plants are sprayed with the preparation of active compound until dripping wet.

The plants are placed in an incubation cabinet at 100% relative atmospheric humidity and at about 20° C.

Evaluation is carried out 3 days after the inoculation.

In this test, a cleary superior activity compared with the prior art is shown, for example, by the compounds according to the following preparation examples: 1 and 2.

It will be appreciated that the instant specification and examples are set forth by way of illustration and not limitation, and that various modifications and changes may be made without departing from the spirit and scope of the present invention.

We claim:

1. An azole-substituted oximino-cyano-acetamide derivative of the formula

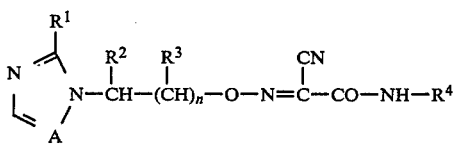

in which
  $R^1$ and $R^3$ each independently is hydrogen or alkyl having up to 3 carbon atoms,
  $R^2$ is hydrogen, alkyl having up to 6 carbon atoms, or halogenoalkyl having up to 2 carbon atoms and up to 5 halogen atoms,
  $R^4$ is hydrogen or CO—NH—$R^5$,
  $R^5$ is hydrogen, cycloalkyl having 3 to 7 carbon carbon atoms, or alkyl having up to 8 carbon atoms and optionally substituted by cyano, hydroxycarbonyl, aminocarbonyl, alkoxy and/or alkoxycarbonyl, each having up to 4 carbon atoms in the alkyl part,
  A is N or CH, and
  n is 0 or 1.

2. A compound according to claim 1, in which
  $R^1$ and $R^3$ each independently is hydrogen or methyl,
  $R^2$ is hydrogen or alkyl having 1 to 4 carbon atoms, and
  $R^5$ is hydrogen, cycloalkyl having 3 to 6 carbon atoms, or alkyl having up to 5 carbon atoms and optionally substituted by cyano or alkoxy having up to 4 carbon atoms.

3. A compound according to claim 2, in which
  $R^1$ and $R^3$ both are methyl,
  $R^2$ is hydrogen, methyl, ethyl, isopropyl or sec.-butyl, and
  $R^5$ is hydrogen or alkyl having up to 3 carbon atoms.

4. A compound according to claim 1, wherein such compound is 2-cyano-2-(triazol-1-yl-methoximino)-acetamide of the formula

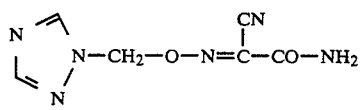

5. A compound according to claim 1, wherein such compound is 2-cyano-2-[2-(triazol-1-yl)-ethyl-oximino] acetamide of the formula

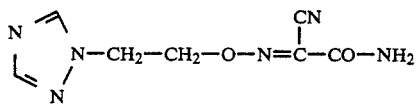

6. A compound according to claim 1, wherein such compound is 1-[2-cyano-2-(triazol-1-yl-methoximino)-acetyl]-urea of the formula

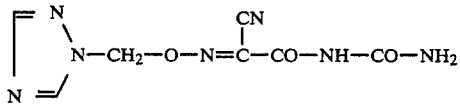

7. A compound according to claim 1, wherein such compound is 2-cyano-2-[1-(triazol-1-yl)-ethyl-oximino]-acetamide of the formula

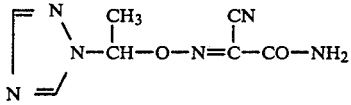

8. A compound according to claim 1, wherein such compound is 2-cyano-2-(imidazol-1-yl-methoximino)-acetamide of the formula

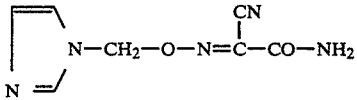

9. A fungicidal composition comprising a fungicidally effective amount of a compound according to claim 1 in admixture with a diluent.

10. A method of combating fungi which comprises administering to such fungi or to a fungus habitat a fungicidally effective amount of a compound according to claim 1.

11. The method according to claim 10, wherein such compound is
2-cyano-2-(triazol-1-yl-methoximino)-acetamide,
2-cyano-2-[2-(triazol-1-yl)-ethyl-oximino]-acetamide,
1-[2-cyano-2-(triazol-1-yl-methoximino)-acetyl]-urea,
2-cyano-2-]1-(triazol-1-yl)-ethyl-oximino]-acetamide or
2-cyano-2-(imidazol-1-yl-methoximino)-acetamide.

* * * * *

UNITED STATES PATENT AND TRADEMARK OFFICE
CERTIFICATE OF CORRECTION

PATENT NO. : 4,518,605
DATED : May 21, 1985
INVENTOR(S) : Wilhelm Brances, et al It is certified that error appears in the above-identified patent and that said Letters Patent is hereby corrected as shown below:

| | |
|---|---|
| Title page, Abstract, line 13 | Delete "hydrocarbonyl" and substitute --hydroxycarbonyl-- |
| Column 9, line 59 | Delete "of" and substitute --or-- |
| Column 11, line 1 | Correct spelling of "acetamide" |

Signed and Sealed this

Twenty-eighth Day of January 1986

[SEAL]

Attest:

DONALD J. QUIGG

Attesting Officer

Commissioner of Patents and Trademarks